(12) United States Patent
Mathey et al.

(10) Patent No.: US 6,417,375 B1
(45) Date of Patent: Jul. 9, 2002

(54) FURYLPHOSPHINES AND ORGANOMETALLIC COMPLEXES CONTAINING THEM

(75) Inventors: Francois Mathey, Paris; Philippe Savignac, Gif-sur Yvette; Frederic Eymery, Alfortville; Paolo Burattin, Lyons, all of (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/700,750

(22) PCT Filed: May 11, 1999

(86) PCT No.: PCT/FR99/01129

§ 371 (c)(1),
(2), (4) Date: Apr. 13, 2001

(87) PCT Pub. No.: WO99/60003

PCT Pub. Date: Nov. 25, 1999

(30) Foreign Application Priority Data

May 20, 1998 (FR) ............................................ 98 06559

(51) Int. Cl.$^7$ .................................................. C07F 9/28
(52) U.S. Cl. ...................................................... 549/216
(58) Field of Search ......................................... 549/216

(56) References Cited

U.S. PATENT DOCUMENTS 5,739,396 A * 4/1998 Trost et al. .................... 564/15
6,133,191 A * 10/2000 Antognazza et al. ......... 502/326
6,153,758 A * 11/2000 Sannicolo et al. ........... 548/111

FOREIGN PATENT DOCUMENTS

EP  0 305 012 A  3/1989
FR  2 314 910 A  1/1977

OTHER PUBLICATIONS

CA 135: 92723, Yeo, Wee–Chuan et al, 2001.*
CA 108: 91576, Prodanchuk, N.G. et al, 1988.*
CA 107: 96792, Brown, John M. et al, 1987.*
CA 105: 209051, Bukachuk, O. M. et al, 1986.*
Farina, V.; "Large Rate Accelarations in the Stille Reaction with Tri–2–furylphosphine and Trifurylarsine as Palladium Ligands: Mechanistic and Synthetic Implications"; Journal of the American Chemical Society, vol. 113, No. 25, 1991, pp. 9585–9595, XP002090428.

* cited by examiner

Primary Examiner—Deborah C. Lambkin
(74) Attorney, Agent, or Firm—Burns, Doane, Swecker & Mathis, L.L.P.

(57) ABSTRACT

The present invention relates to novel water-soluble furylphosphines.

It also relates to organometallic complexes comprising these furylphosphines and to the use of such complexes.

It also relates to the process for the preparation of the water-soluble furylphosphines.

10 Claims, No Drawings

FURYLPHOSPHINES AND ORGANOMETALLIC COMPLEXES CONTAINING THEM

This application is a 371 of PCT/FR99/01129, May 11, 1999.

The present invention relates to novel water-soluble furylphosphines.

It also relates to organometallic complexes comprising these furylphosphines and to the use of such complexes.

It also relates to the process for the preparation of the water-soluble furylphosphines.

Unsubstituted trifurylphosphines are described in an article by V. Farina and B. Krishnan published in the Journal of the American Chemical Society, 1991, 113, pages 9585–9595. According to this article, systems comprising these trifurylphosphines exhibits a notable catalytic activity.

The prior art does not disclose water-soluble furylphosphines such as those forming the subject-matter of the present invention.

The novel water-soluble furylphosphines correspond to the general formula (I):

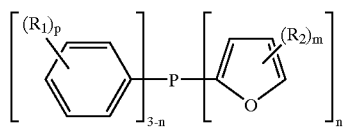

in which:

n represents an integer from 1 to 3, at least one $R_2$ radical represents a hydrophilic group, such as —$SO_2M$, —$SO_3M$, —$CO_2M$ or —$PO_3M$, M representing an inorganic or organic cationic residue chosen from a proton, cations derived from alkali metals or alkaline earth metals, ammonium cations —$N(R)_4$, in the formula of which the R symbols, which are identical or different, represents a hydrogen atom or an alkyl radical having from 1 to 12 carbon atoms, or other cations derived from metals having furylsulphinic acid. furylcarboxylic acid, furylsulphonic acid or furylphosphonic acid salts which are soluble in water.

$N(R)_3X$, in the formula of which the R symbols, which are identical or different, represent a hydrogen atom or an alkyl radical having from 1 to 12 carbon atoms and X represents an organic or inorganic anion.

—OH, $R_1$ represents a hydrophilic group as defined for $R_2$ or an alkyl or alkoxy group having 1 to 12 carbon atoms, a halogen atom, a nitrile group or a haloalkyl group having 1 to 12 carbon atoms, m represents 1 or 2, p represents an integer from 0 to 3, when m is equal to 2, an $R_2$ radical can represent an alkyl or alkoxy group having 1 to 12 carbon atoms, a halogen atom, a nitrile group or a haloalkyl group having 1 to 12 carbon atoms.

The term "water-soluble" or the expression "soluble in water" is understood to mean, in the present text, a compound soluble to at least 0.01 g per liter of water.

The water-soluble furylphosphines of the invention are generally compounds of general formula (I) in which:

n represents an integer from 1 to 3, $R_2$ represents a hydrophilic group, such as —$SO_2M$, —$SO_3M$, —$CO_2M$ or —$PO_3M$, M representing an inorganic or organic cationic residue chosen from a proton, cations derived from alkali metals or alkaline earth metals, ammonium cations —$N(R)_4$, in the formula of which the R symbols, which are identical or different, represent a hydrogen atom or an alkyl radical having from 1 to 4 carbon atoms, or other cations derived from metals having furylsulphinic acid, furylcarboxylic acid, furylsulphonic acid or furylphosphonic acid salts which are soluble in water, m represents 1 or 2, $R_1$ represents a hydrophilic group as defined for $R_2$ or an —$N(R)_3X$ substituent, in the formula of which the R symbols, which are identical or different, represent a hydrogen atom or an alkyl radical having from 1 to 4 carbon atoms and X represents an organic or inorganic anion, an —OH substituent, an alkyl or alkoxy substituent having 1 to 4 carbon atoms, a halogen atom, a nitrile group or a trifluoroalkyl group, p represents an integer from 0 to 2.

Another subject-matter of the present invention is the preparation of the novel water-soluble furylphosphines. This preparation is generally carried out starting with a precursor, such as diphenylfurylphosphine or phenyldifurylphosphine or trifurylphosphine, which is unsubstituted by hydrophilic groups. In consists in introducing $R_2$ hydrophilic groups onto the furyl rings and, optionally, $R_1$ groups onto the phenyl rings.

For example, furylphoshphines of formula (I) can thus generally be prepared by coupling an organolithium compound, the organic part of which corresponds to a compound of general formula (I) which does not comprise $R_2$ substituents and which is bonded to the lithium atom via its furyl ring or rings, to the electrophilic centre of an $R_2$ precursor, such as, for example, sulphur dioxide, carbon dioxide, alkyl chlorophosphates, pyridine sulphonates or trialkylamine sulphonates.

The organolithium compound is itself obtained by the action of a lithiated base (for example butyllithium) on the precursor furylphosphine.

Reference may be made, for the preparation of the precursor furylphosphines, to, for example, the article by A. J. Zapata and A. C. Rodon in Org. Prep. Proced. Int., 27, 5 (1995), pages 567 et seq.

Water-soluble furylphosphines make it possible to prepare organometallic complexes which comprise at least one water-soluble furylphosphine of formula (I) and at least one metal.

The metals which can be completed by water-soluble furylphosphines are generally all the transition metals from Groups 1b, 2b, 3b, 4b, 5b, 6b, 7b and 8 of the Periodic Classification of the Elements as published in "Handbook of Chemistry and Physics, 51st Edition (1970–1971)" of The Chemical Rubber Company.

Mention may more particularly be made, among these metals, of the metals which can be used as catalysts of chemical reactions. Thus, mention may, of non-limiting examples, of nickel, cobalt, iron, ruthenium, rhodium, palladium, osmium, iridium, platinum, copper, silver, gold, zinc, cadmium or mercury.

The organometallic complexes comprising the water-soluble furylphosphines can be prepared by bringing a solution of a compound of the chosen metal into contact with an aqueous solution of the water-soluble furylphosphine of formula (I).

The compound of the metal can be dissolved in water or in an organic solvent, it being possible for the said organic solvent itself to be miscible or immiscible with water.

The metal, in the compound employed, can either be at the degree of oxidation which it will have in the organometallic complex or at a higher degree of oxidation.

It may be indicated, by way of examples, that, in the organometallic complexes of the invention, rhodium is at the degree of oxidation (I), ruthenium at the degree of oxidation (II), platinum at the degree of oxidation (I), palladium at the degree of oxidation (II), osmium at the degree of oxidation (O), iridium at the degree of oxidation (O) and nickel at the degree of oxidation (O).

If during the preparation of the organometallic complex, the metal is employed at a higher degree of oxidation, it will have to be reduced in situ.

Organometallic complexes comprising the water-soluble furylphoshphines of formula (I) can be used as catalysts of chemical reactions.

In aqueous two-phase catalysis, the water-soluble furylphosphines benefit from the synergy between the natural hydrophilicity of the furyl ring and that of the $R_2$ radical or radical. They achieve very high solubility values in water.

Mention maybe made, as chemical reactions which can be catalysed by organometallic complexes comprising the water-soluble furylphosphines of formula (I), of, for example the hydroformylation and the hydrocarbonylation of olefins in the presence of rhodium complexes, the hydrogenation of olefins, aldehydes, acids, enamides and nitroaromatic compounds in the presence of ruthenium, rhodium, platinum or palladium complexes, the terrorization of dienes, the isomerization of olefins, the dimerization of ethylene or of acrylonitrile, the hydrocyanation of olefins in the presence of nickel complexes, the synthesis of furan in the presence of ruthenium complexes, the metathesis of olefins in the presence of ruthenium complexes, the polymerization of acrylates in the presence of nickel complexes or carbon-carbon coupling reactions, such as, for example, the Heck or Suzuki reaction, in the presence of nickel or palladium complexes.

The compounds of the invention are in particular of use in the isomerization reaction of nitriles obtained by hydrocyanation of a diene and more particularly the isomerization of 2-methyl-3-butenenitrile to 3-pentenenitrile. This reaction has great industrial importance in the process for the manufacture of adiponitrile. The latter is a major synthetic intermediate in, in particular, the manufacture of monomers for polyamides, such as caprolactam or hexamethylenediamine.

The examples which follow illustrate the invention.

EXAMPLES 1 to 4 : synthesis of water-soluble furylphosphines of formula (I)

Example 1: sodium 2-(diphenylphosphino)furan-5-carboxylate 30.3 ml (47 mmol) of n-butyllithium (assaying at 1.55M) are charged to a 500 ml four-necked round-bottomed flask purged beforehand with nitrogen and surmounted by a pressure-equalizing dropping funnel, by a reflux condenser equipped with a bubbler, by a mechanical stirrer and by a thermometer and then 6.4 ml (42 mmol) of tetramethylethylenediamine (TMEDA), in 50 ml of anhydrous ethyl ether degassed with nitrogen, are rapidly incorporated. 10.65 g (42.3 mmol) of diphenylfurylphosphine, dissolved beforehand in 50 ml of anhydrous ethyl ether degassed with nitrogen, are run in dropwise, the temperature being allowed to rise to 35° C. The mixture turns orange in colour.

After stirring for 15 min under a stream of nitrogen, the formation of the anion is monitored by $^{31}P$ NMR. This formation is complete 15 min after the end of addition of the phosphine.

In place of the reflux condenser, a tube is then fitted which allows the solution to be transferred dropwise into a Dewar flask comprising solid carbon dioxide immersed in approximately 200 ml of anhydrous ethyl ether degassed with nitrogen. The anion immediately couples to give a white precipitate. After leaving overnight exposed to the open air, the white solid, in suspension in ether, is taken up in 100 ml of a saturated $NaHCO_3$ solution and the combined mixture is extracted. The ethereal phase is further extracted with two times 30 ml of degassed water. The aqueous phases are combined and acidified under cold conditions with small portions of 12N HCl to neutral pH. This aqueous phase is extracted with three times 50 ml dichloromethane. The organic phases are combined and 1.49 g of sodium hydroxide, dissolved in a few ml of water, are added to them. After evaporation of the solvents, a viscous yellow-brown oil is obtained, which oil is converted to a fine white powder after several trituration and washing operations in anhydrous ethyl ether and after drying at 90° C. under vacuum. 11.44 g of the desired product (36 mmol) are recovered, i.e. a yield of 85%.

It is characterized by:

$^{31}P$ NMR ($D_2O$): $\delta=25.1$ $^2H$ NMR ($D_2O$): $\delta=6.20$ (d, 1H, $^3J_{HH}=3.2$, $C_3\underline{H}$), $\delta=6.81$ (m, 1H, $C_4\underline{H}$), $\delta=7.06$ (m, 10H, Ar)

$^{13}C$ NMR ($D_2O$): $\delta=117.8$ (s, $\underline{C}_3H$), $\delta=124.9$ (m, $\underline{C}_4H$), $\delta=131.1$ (d, $^3J_{CP}=7.0$, $\underline{C}_{meta}$), $\delta=131.7$ (s, $\underline{C}_{para}$), $\delta=135.5$ (d, $^2J_{CP}=19.7$, $\underline{C}_{ortho}$), $\delta=136.8$ (d, $^1J_{CP}=4.4$, $\underline{C}_{ipso}$), $\delta=156.4$ (s, $\underline{C}OO$), $\delta=156.9$ (d, $^1J_{CP}=13.7$, $\underline{C}_5H$), $\delta=168.1$ (s, $\underline{C}_2H$).

The solubility of this furylphosphine in water is 250 g/l at 23° C.

Example 2: disodium 2-(diphenylphosphino)furan-5-phosphonate 33.8 ml (52 mmol) of n-butyllithium (assaying at 1.55M) are charged to a 500 ml four-necked round-bottomed flask purged beforehand with nitrogen and surmounted by a pressure-equalizing dropping funnel, by a reflux condenser equipped with a bubbler, by a mechanical stirrer and by a thermometer and then 6.4 ml (42 mmol) of TMEDA, in 50 ml of anhydrous ethyl ether degassed with nitrogen, are rapidly incorporated. 12.32 g (48.9 mmol) of diphenylfurylphosphine, dissolved beforehand in 40 ml of anhydrous ethyl ether degassed with nitrogen, are run in dropwise, the temperature being allowed to rise to 35° C. The mixture turns orange in colour.

After stirring for 15 min under a stream of nitrogen, the formation of the anion is monitored by $^{31}P$ NMR. This formation is complete 15 min after the end of addition of the phosphine.

The reaction mixture is cooled to −70° C. and a tube is fitted in place of the reflux condenser. The solution is transferred dropwise into a second four-necked reactor, equipped with the same devices as the first, which is cooled to −60° C. and which comprises 7.3 ml (49 mmol) of diethyl chlorophosphate diluted in 20 ml of anhydrous ethyl ether. The mixture is allowed to return to room temperature before being hydrolysed in situ with 100 ml of an aqueous ammonium chloride solution. Extraction is then carried out with three times 50 ml ethyl ether. The organic phases are combined and dried over Mg sulphate. The solution is filtered and evaporated to produce 20 g of a yellow-brown oil. The latter is heated at 100° C. under $10^{-2}$ mm of mercury (1.3 Fa) in a bulb oven in order to remove the phosphates. 17.2 g of a viscous yellow-brown oil are recovered, which oil is subsequently chromatographed on 10 cm of silica gel with a 50/50 ethyl acetate/hexane mixture as eluent. After evaporation of the solvents, 14.2 g of a coloured oil are collected, which oil is placed overnight in solution in 60 ml of dichloromethane, with magnetic stirring, in the presence of 10 ml (74 mmol) of bromotrimethylsilane. The reaction is exothermic and the mixture is observed to decolour. After evaporation of the solvents, the product is taken up in 60 ml of acetone and 2 ml of distilled water. After 2 h 30, the solvents are evaporated and the product is taken up in the minimum amount of methanol, 3.04 g of sodium hydroxide, in 40% aqueous solution, are incorporated with stirring under cold conditions. A white precipitate is formed. The solvents are evaporated and the product is washed with acetone, filtered off and dried at 100° C. under vacuum. The desired product is recovered with a yield of 54%..

It is characterized by:

$^{31}$P NMR (D$_2$O): δ=28.2, δ=0.8 (P=O)

$^1$H NMR (D$_2$O): δ=6.72 (m, 2H, C$_3\underline{H}$, C$_4\underline{H}$), δ=7.41 (m, 10H, Ar)

$^{13}$C NMR (D$_2$O): δ=117.9 (dd, $^4J_{CF}$=4.67, $^3J_{CP}$=20.0, $\underline{C}_3$H), δ=124.6 (dd, J$_{CP}$=3.5, J$_{CP}$=21.0, $\underline{C}_4$H), δ=131.6 (d, $^3J_{CP}$=7.5, $\underline{C}_{meta}$), δ=132.2 (s, $\underline{C}_{para}$), δ=135.8 (d, $^2J_{CP}$=19.2, $\underline{C}_{ortho}$), δ=137.8 (s, $\underline{C}_{ipso}$), δ=155.4 (dd, J$_{CP}$=7.4, J$_{CP}$=10.4, $\underline{C}_5$H), δ=165.1 (J$_{CP}$=199.0 ($\underline{C}_2$H).

The solubility of this furylphosphine in water is 680 g/l at 20° C.

Example 3: tetrasodium 2,2'-phenylphosphine-diylbis(furan-5-phosphonate)

42 ml (65 mmol) of n-butyllithium (assaying at 1.55M) are charged to a 500 ml four-necked round-bottomed flask purged beforehand with nitrogen and surmounted by a pressure-equalizing dropping funnel, by a reflux condenser equipped with a bubbler, by a mechanical stirrer and by a thermometer and then 9.15 ml (60 mmol) of TMEDA, in 50 ml of anhydrous ethyl ether degassed with nitrogen, are rapidly incorporated. 4.41 ml (60.0 mmol) of furan, diluted beforehand in 40 ml of anhydrous ethyl ether degassed with nitrogen, are run in dropwise, the temperature being allowed to rise to 35° C. over 30 min. The mixture turns orange in colour.

The mixture is cooled to −40° C. in order to run in dropwise 4.2 ml (30 mmol) of dichlorophenylphosphine diluted in 20 ml of ether. After monitoring the formation of the product by $^{31}$P NMR, the mixture is returned to room temperature in order to incorporate 9.15 ml (60 mmol) of TMEDA in 50 ml of ethyl ether, and then 42 ml (65 mmol) of n-butyllithium (assaying at 1.55M) are run in rapidly. After stirring for 15 min under a stream of nitrogen, the formation of the anion is monitored by $^{31}$P NMR. This formation is complete 15 min after the end of addition of the phosphine.

The reaction mixture is cooled to —70° C. and a tube is fitted in place of the reflux condenser. The solution is transferred dropwise into a second four-necked reactor, equipped with the same devices as the first, which is cooled to −60° C. and which comprises 8.95 ml (60 mmol) of diethyl chlorophosphate diluted in 20 ml of anhydrous ethyl ether. The mixture is allowed to return to room temperature before being hydrolysed in situ with 100 ml of an aqueous ammonium chloride solution. The mixture is then extracted with three times 50 ml ethyl ether. The organic phases are combined and dried over Mg sulphate. The solution is filtered and evaporated to produce 20 g of a red-brown oil. The latter is heated at 100° C. under 10$^{-2}$ mm of mercury (1.3 Pa) in a bulb oven in order to remove the phosphates. The product is subsequently chromatographed on 10 cm of silica gel with ethyl acetate as eluent. Difurylphenylphosphine and monophosphorylated compound are thus removed. After evaporation of the solvents, 3.5 g of pure product are collected (yield: 23%). The entire reaction is repeated a second time in order to obtain sufficient product for the continuation of the synthesis.

8.55 g (16.6 mmol) of diphosphorylated compound are placed overnight in solution in 50 ml of dichloromethane, with magnetic stirring, in the presence of 9.43 ml (70 mmol) of bromotrimethylsilane. The reaction is exothermic and the mixture is observed to decolour. After evaporation of the solvents, the product is taken up in 50 ml of acetone and 2 ml of distilled water. After 2 h 30, the solvents are evaporated and the product is taken up in the minimum amount of methanol. 2.8 g of sodium hydroxide, in 40% aqueous solution, are incorporated with stirring under cold conditions. The mixture darkens from yellow to brown. The solvents are evaporated and the resulting orange solid is triturated and washed with acetone, filtered off and dried at 100° C. under vacuum. 6.7 g of the desired product, of-white in colour, are recovered with a yield of 82% (with respect to the diphosphorylated compound).

It is characterized by:

$^{31}$P NMR (D$_2$O): δ=49.5, δ=0.0 (P=O)

$^1$H NMR (D$_2$O): δ=6.67 (m, 2H, C$_4\underline{H}$), δ=6.80 (m, 2H, C$_3\underline{H}$), δ=7.41 (m, 5H, Ar)

$^{13}$C NMR (D$_2$O): δ=117.7 (d, $^3J_{CP}$=20.4, $\underline{C}_3$H), δ=123.9 (dd, $^3J_{CPO}$=9.2, $^2H_{CP}$=18.3, $\underline{C}_4$H), δ=131.4 (d, $^3J_{CP}$=7.0 $\underline{C}_{meta}$), δ=131.9 (s, $\underline{C}_{para}$), δ=134.7 (d, $^2J_{CP}$=19.0, $\underline{C}_{ortho}$), δ=136.9 (s, $\underline{C}_{ipso}$), δ=153.5 (d, $^1J_{CP}$=7.3, J$_{CP}$=10.4, $\underline{C}_5$H), δ=164.5 (d, $^1J_{CPO}$=189.5, C$_2$H).

The solubility of this furylphosphine in water is 1140 g/l at 23° C.

Example 4: sodium 2-(diphenylphosphino)furan-5-sulphinate 26.3 ml (40 mmol) of n-butyllithium (assaying at 1.52M) are charged to a 500 ml four-necked round-bottomed flask purged beforehand with nitrogen and surmounted by a pressure-equalizing dropping funnel, by a reflux condenser equipped with two bubblers (water and silicone oil), by a mechanical stirrer and by a thermometer and then 10.65 g (42.3 mmol) of diphenylfuryphosphine, dissolved beforehand in 50 ml of anhydrous ethyl ether degassed with nitrogen, are in in dropwise, the temperature being allowed to rise to 30° C. The mixture turns yellow in colour.

After stirring for 45 min under a stream of nitrogen, the formation of the anion is monitored by $^{31}$P NMR. The reaction mixture is cooled to −60° C. and the stream of nitrogen is replaced by a stream of sulphur dioxide. A white precipitate appears and then the mixture turns yellow in colour and subsequently brown. The reaction is exothermic. A strong stream of nitrogen is subsequently reestablished in order to degas the reactor and the mixture is allowed to slowly return to room temperature. 100 ml of degassed water are subsequently added in situ and the mixture is left stirring for one hour. Extraction is carried out three times with water. The aqueous phases are combined, cooled with an ice bath and acidified with 10 ml of 3N HCl in the presence of 100 ml of dichloromethane. The yellow colour disappears. Extraction is then rapidly carried out three times with dichloromethane. The organic phases are combined and 1.2 g of sodium hydroxide are incorporated with stirring under cold conditions. The solvents are evaporated under vacuum, the temperature being limited to a maximum of 40° C. 6.86 g (20.3 mmol) of the desired product (white solid) are obtained; the yield is 51%.

The product is characterized by:

$^{31}$P NMR (D$_2$O): δ=26.7

$^1$H NMR (D$_2$O): δ=6.40 (m, 1H, C$_3$H), δ=6.53 (m, 1H, C$_4$H), δ=7.06 (m, 10H, Ar)

$^{13}$C NMR (D$_2$O): δ=111.6 (s, C$_3$H), δ=124.8 (m, C$_4$H), δ=131.1 (d, $^3$J$_{CP}$=7.0 C$_{meta}$), δ=131.7 (s, C$_{para}$), δ=135.5 (d, $^2$J$_{CP}$=19.4, C$_{ortho}$), δ=136.8 (d, $^1$J$_{CP}$=2.9, C$_{ipso}$), δ=156.5 (d, J$_{CP}$=16.5 C$_5$H), δ=170.1 (s, C$_2$H).

The solubility of this furylphosphine in water is 205 g/l at 21° C.

A pressure of 3 to 4 bar (0.3 to 0.4 MPa) of hydrogen is established and the mixture is stirred for a variable time (see Table 2 below) depending on the nature of the furylphosphine and the absorption of gas. At the end of the test, after degassing, the reaction mixture is evaporated to dryness and analysed by $^1$H NMR in d$_6$-dimethyl sulphoxide.

The characteristics of the various examples (reference of the complex, organometallic complex/substrate to be hydrogenated ratio by weight in %, H$_2$ pressure, duration) and the results obtained (degree of conversion of the substrate) are collated in Table 2 below.

TABLE 2

| Examples | Complex (example reference) | Complex, % by weight | Methanol/water ratio | H$_2$ Pressure | Duration | Degree of conversion |
|---|---|---|---|---|---|---|
| Ex. 9 | Example 5 | 1.25 | 1/2 | 4.0 bar | 3h 30 | 66% |
| Ex. 10 | Example 5 | 1.25 | 1/1 | 3.0 bar | 4h 30 | 95% |
| Ex. 11 | Example 7 | 1.25 | 1/1 | 3.1 bar | 2h | 100% |
| Ex. 12 | Example 6 | 0.5 | 1/1 | 3.0 bar | 18h 30 | 8% |
| Ex. 13 | Example 8 | 1.25 | 1/1 | 3.1 bar | 2h | 100% |

EXAMPLES 5 to 13: preparation of metal complexes of water-soluble furylphosphines of formula (I) and use of these complexes as hydrogenation catalysts The preparation is carried out in a 50 ml autoclave, the walls of which are coated with Teflon® and which is equipped with a magnetic bar, a safety valve, a manometer, a valve for delivering gas and a valve for introducing liquid.

The various rhodium complexes (Examples 5 to 8), which will subsequently be used as catalysts for the hydrogenation of Z-α-acetamidocinnamic acid (Examples 9 to 13), are first of all prepared.

The preparation of the rhodium complexes consists in stirring, for 10 min under an argon atmosphere, a solution, in 2 ml of water, of 0.05 mmol of one of the water-soluble furylphosphines prepared in Examples 1 to 4, which solution is mixed with a solution, in 1 ml of acetone, of 0.025 mmol of [Rh(COD)$_2$]$^-$PF$_6^-$ (COD=cyclooctadiene). After the colouring of the mixture has changed from orange to yellow, monitoring is carried out by $^{31}$P NMR.

The characteristics of the Rh complexes prepared are collated in Table 1 below.

TABLE 1

| Examples | Furyl-phosphine | Appearance | δ $^{31}$P (in ppm) | J$_{RH-P}$ (Hz) |
|---|---|---|---|---|
| Ex. 5 | Example 1 | clear vivid yellow | 14.6 (d) | 144 |
| Ex. 6 | Example 4 | clear vivid yellow | 15.0 (d) | 148 |
| Ex. 7 | Example 2 | clear vivid yellow | 12.0 (d, P$_{III}$) −1.7 (s, P = O) | 148 |
| Ex. 8 | Example 3 | clear vivid yellow | −1.0 (s, P = O) −4.0 (d, P$_{III}$) | 150 |

The complex prepared above is introduced into the autoclave using a syringe, followed by a solution of 0.410 g (2 mmol) of Z-α-acetamidocinnamic acid in 30 ml of methanol and of water (in proportions by volume of 1/1 or 1/2).

The mixture remains homogeneous.

EXAMPLES 14 to 16: preparation of metal complexes of water-soluble furylphoshines of formula (I) and use of the said complexes in the hydroformylation of styrene Preparation of the complexes The organometallic complex is preformed by the dropwise addition of the furylphosphine of formula (I), dissolved in 1 ml of water, to the metal precursor [Rh(CO)$_2$Cl]$_2$ or [Rh(CO)$_2$acac], the abbreviation "acac" meaning "acetylacetonate", in solution either in 1 ml of acetone (alternative form (a) in Table 3 below), which leads to a resulting homogeneous medium, or in 1 ml of toluene (alternative form (b) in Table 3 below), which leads to a resulting heterogeneous medium (two-phase medium).

When the preparation is carried out in heterogeneous medium, transfer of the yellow colouring from the organic phase to the aqueous phase is observed and the solution obtained is clear.

When the preparation is carried out in homogeneous medium, a portion of the metal reprecipitates in the form of metal-green needles and the colour of the medium is yellowish, indeed even black.

The use as precursor of the dimer [Rh(CO)$_2$Cl]$_2$ requires the addition of triethylamine (0.1 ml).

The complexes thus prepared were analysed by $^{31}$P NMR at room temperature. They all result in a spectrum exhibiting a broad peak (characteristic of complexing with rapid exchange of ligands) with a chemical shift δ=−10 to +20 ppm, according to the phosphine used.

Hydroformylation of styrene

A 250 ml autoclave, equipped with a magnetic bar, a safety valve, a manometer and two valves for delivering gas, is purged with argon. Toluene and distilled water, both degassed beforehand under nitrogen, and then the catalyst (organometallic complex) are successively introduced, with a pipette, under a stream of argon.

Two test alternative forms were carried out:

alternative form (a), with 8 ml of water/8 ml of toluene/2 g of styrene, on the one hand, and 1 ml of acetone/1 ml of distilled water/0.08 mmol of Rh/0.16 mmol of furylphosphine, on the other hand, alternative form (b), with 2.5 ml of water/2.5 ml of toluene/1 g of styrene, on the one hand, and 1 ml of toluene/1 ml of distilled water/0.04 mmol of Rh/0.08 mmol of furylphosphine, on the other hand.

A pressure of 10 bar (1 MPa) of carbon monoxide and of 10 bar (1 MPa) of hydrogen is established. The reaction mixture is heated at the temperature (T°C) with vigorous magnetic stirring for 18 h.

After ventilating off the excess gas, the reaction mixture is separated by settling into two phases and the organic phase is analysed by gas phase chromatography. The results are collated in Table 3 below: yield (Yd) of aldehyde and branched aldehyde/linear aldehyde (bA/lA) ratio.

TABLE 3

| Example | Phosphine (Example) Precursor | Alternative form | T° C. | Yd | bA/lA |
|---|---|---|---|---|---|
| Example 14 | prepared [Rh(CO)$_2$Cl]$_2$ Example 1 | (a) | 55° C. | 32% | 86/14 |
| Example 15 | prepared [Rh(CO)$_2$acac] Example 2 | (a) | 65° C. | 100% | 83/17 |
| Example 16 | prepared [Rh(CO)$_2$acac] Example 4 | (b) | 50° C. | 69% | 81/19 |

EXAMPLES 17 to 26c : Use of metal complexes with different ligands in carbon-carbon coupling reactions in aqueous medium (Heck Reaction)

2 mmol (0.42 g) of iodobenzene, 3 mmol (0.30 g) of ethyl acrylate, 3 mmol (0.31 g) of triethylamine and 3 ml of acetonitrile are introduced into a Schlenk tube equipped with a magnetic bar and under an argon atmosphere.

0.05 mmol (11.2 g) of Pd(O$_2$CCH$_3$)$_2$ is added to the medium, followed by a phosphinic ligand (0.15 mmol) in the form dissolved in 0.5 ml of water.

The mixture is heated to a predetermined temperature with vigorous stirring in order to obtain homogenization of the medium.

At the end of the reaction, the solution is filtered and then transferred into a funnel in order to be separated by settling.

After washing several times with water and with ethylether, the compounds formed are extracted with ether.

After evaporation of the solvents, a brown oil is collected.

The degree of conversion of the iodobenzene is determined by proton NMR analysis of the brown oil collected.

The nature of the ligands used, the reaction temperature and the reaction time are shown in Table 4 below. The degree of conversion of the iodobenzene to ethyl cinnamate is also specified in this table. The various ligands used are:

Ligand A : dilithium 2,2'-phenylphosphine-diylbis(furan-5-sulphinate)

Ligand B : disodium 2-(diphenylphosphino)furan-5-phosphonate)

Ligand C : sodium 2-(diphenylphosphino)furan-5-carboxylate

Ligand D : dilithium 2,2'-phenylphosphine-diylbis(furan-5-carboxylate)

Ligand E : trisodium meta-triphenylphospine-trisulphonate (ligand of the prior art)

TABLE 4

| Example | 17 | 18 | 19 | 20 | 21 | 22 | 23 | 24 | 25c | 26c |
|---|---|---|---|---|---|---|---|---|---|---|
| Ligands | A | | B | | C | | D | | E | |
| T ° C. | 22 | 80 | 40 | 70 | 40 | 80 | 40 | 80 | 40 | 70 |
| Duration (hours) | 10 | 2.5 | 2 | 1 | 2 | 1 | 2 | 1 | 2 | 1 |
| Degree of conversion of the iodobenzene (%) | 65 | 100 | 100 | 100 | 55 | 90 | 99 | 100 | 21 | 100 | the ligands in accordance with the invention therefore make it possible to obtain a degree of conversion of the iodobenzene at temperatures which are not very high and even at room temperature.

EXAMPLES 27 to 29c : Use of metal complexes with different ligands in the isomerization reaction of 2-methyl-3-butenenitrile (2M3BN) to 3-pentenenitrile (3PH)

1.5 g of aqueous solution of a water-soluble ligand L, with a concentration expressed in mmol/kg of ligand, are introduced into a Schlenk tube equipped with a magnetic bar and under an argon atmosphere.

5 g of 2M3BN and then 40 to 45 mg of bis(1,5-cyclooctadiene)nickel(0) (Ni(COD)$_2$) are added in order to obtain, in the mixture, a Ligand/Nickel molar ratio equal to 4.5. The stirred mixture is brought to 90° C. and maintained at this temperature for 3 hours. After cooling, the reaction mass is dissolved in acetone and analysed by Gas Phase Chromatography in order to quantitatively determine the organic compounds present. The results obtained with several ligands, two of which in accordance with the invention, are collated in Table 5 below.

TABLE 5

| Example | 27 | 28 | 29c |
|---|---|---|---|
| Ligands | dilithium 2,2'-phenylphosphine-diylbis-(furan-5-sulphinate) | tetrasodium 2,2'-phenylphosphine-diylbis-(furan-5-sulphinate) | Na, TPPTS |
| Concentration ligand L (mmol/kg) | 500 | 800 | 500 |
| Ligand/Ni ratio | 4.5 | 4.5 | 4.5 |
| Degree of conversion of the 2M3BN (%) | 20 | 87 | 68 |
| 3PN Yield (%) | 73 | 92 | 87 |

TPPTS: meta-triphenylphosphinetrisulphonate

The ligands of the invention make it possible to obtain high degrees of conversion of the 2M3BN with good selectivity for 3PN.

In Tables 4 and 5, Examples 25c 26c and 29c are comparative example carried out with a ligand of the prior art.

What is claimed is:
1. A water-soluble furylphosphine corresponding to the general formula (I):

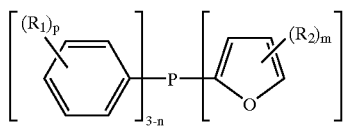

in which:
a represents an integer from 1 to 3,
at least one $R_2$ radical represents a hydrophilic group comprising:
—$SO_2M$, —$SO_3M$, —$CO_2M$ or —$PO_3M$, M representing an inorganic or organic cationic residue comprising a proton, cations derived from alkali metals or alkaline earth metals, ammonium cations —$N(R)_4$ in the formula of which the R symbols, which are identical or different, represent a hydrogen atom or an alkyl radical having from 1 to 12 carbon atoms or the other cations derived from metals the salts of furylsulphinic acid, of furylcarboxylic acid, of furylsulphonic acid or of furylphosphonic acids of which are water-soluble.
$N(R)_3X$, in which formula the symbols R, which are identical or different, represent a hydrogen atom or an alkyl radical containing from 1 to 12 carbon atoms, X represents an organic or inorganic anion,
—OH,
$R_1$ represents a hydrophilic group according to the definition given for $R_2$ or an alkyl or alkoxy group containing 1 to 12 carbon atoms; a halogen atom, a nitrile group or a haloalkyl group containing 1 to 12 carbon atoms,
m represents 1 or 2,
p represents an integer from 0 to 3,
when m is equal to 2, an $R_2$ radical can also represent an alkyl or alkoxy group containing 1 to 12 carbon atoms, a nitrile group or a haloalkyl group containing 1 to 12 carbon atoms.

2. Water-soluble furylphosphines according to claim 1, corresponding to the general formula (I), in which:
n represents an integer from 1 to 3,
$R_2$ represents a hydrophilic group comprising:
—$SO_2M$, —$SO_3M$, —$CO_2M$ or —$PO_3M$, M representing an inorganic or organic cationic residue comprising a proton, cations derived from alkali metals or alkaline-earth metals, ammonium cations —$N(R)_4$ in which formula the symbols R, which may be identical or different, represent a hydrogen atom or an alkyl radical having from 1 to 4 carbon atoms, the other cations derived from metals, the salts of furylsulphinic acids, of furylcarboxylic acids, of furylsulphonic acids or of furylphosphonic acids of which are water-soluble.
m represents 1 or 2,
$R_1$ represents a hydrophilic group according to the definition given for $R_2$, or a substituent: $N(R)_3X$, in which formula the symbols R, which may be identical or different, represent a hydrogen atom or an alkyl radical containing from 1 to 4 carbon atoms and X represents an organic or inorganic anion or an —OH substituent or an alkyl or alkoxy substituent containing 1 to 4 carbon atoms, a halogen atom, a nitrile group or a trifluoroalkyl group,
p represents an integer from 0 to 2.

3. Process for preparing water-soluble furylphoshphines according to claim 1, comprising carrying out a condensation of an organolithium compound, the organic portion of which corresponds to a compound of general formula (I) containing no substituents $R_0$ and which is linked to the lithium atom via its furyl ring(s), with a precursor of the group $R_2$ comprising sulphur dioxide, carbon dioxide, alkyl chlorophosphates, pyridine sulphonates or trialkylamine sulphonates.

4. Organometallic complexes comprising at least one waste-soluble furylphosphine according to claim 1 and at least one metal selected from the transition metals from groups 1b, 2b, 3b, 4b, 5b, 6b, 7, and 8 of the Periodi Table of the Elements.

5. Organometallic complexes according to claim 4, comprising at least one metal selected from nickel, cobalt, iron, ruthenium, rhodium, palladiium, osmium, iridium, platinum, copper, silver, gold, zinc, cadmium and mercury.

6. Process for preparing organometallic complexes according to claim 4, comprising placing a solution of a compound of said metal in contact with an aqueous solution of the water-soluble furylphosphine of formula (I).

7. Preparation process according to claim 6, comprising dissolving the metal compound in water or in an organic solvent, said organic solvent itself possibly being miscible or immiscible with water.

8. Preparation process according to claim 1, wherein the metal in the compound used is either in the oxidation state which it will have in the organometallic complex or in a higher oxidation state with an in-situ reduction.

9. Process according to claim 8, wherein, if the metal is in a higher oxidation state, an in-situ reduction of said metal is carried out.

10. A method for the catalysis of hydroformylation and hydrocarbonylation reactions of olefins in the presence of rhodium complexes, hydrogenation reactions of olefins, aldehydes, acids, enamides and nitroaromatic compounds in the presence of ruthenium, rhodium, platinum or palladium complexes, telomerization reactions of dienes, isomerization reactions of olefins, dimerization reactions of ethylene or of acrylonitrile, hydrocyanation reactions of olefins in the presence of nickel complexes, furan synthesis reactions in the presence of ruthenium complexes, metathesis reactions of olefins in the presence of ruthenium complexes, and polymerization reactions of acrylates in the presence of nickel complexes comprising using an effective amount of the organometallic complex according to claim 4.

* * * * *